United States Patent [19]

Hansen, Jr.

[11] Patent Number: 4,577,964
[45] Date of Patent: Mar. 25, 1986

[54] APPARATUS AND METHOD FOR DETECTING PLATELETS IN WHOLE BLOOD

[75] Inventor: William P. Hansen, Jr., Middleborough, Mass.

[73] Assignee: Ortho Diagnostics, Inc., Raritan, N.J.

[21] Appl. No.: 939,943

[22] Filed: Sep. 6, 1978

[51] Int. Cl.$^4$ .................. G01N 33/48; G01N 21/00
[52] U.S. Cl. ................................. 356/39; 356/338; 356/343; 356/336
[58] Field of Search ............... 356/39, 337, 338, 341, 356/343, 336; 250/576

[56] References Cited

U.S. PATENT DOCUMENTS 4,110,604  8/1978  Haynes et al. .................. 324/71
4,202,625  5/1980  Weiner et al. .................. 356/39

Primary Examiner—Rodney B. Bovernick
Attorney, Agent, or Firm—Mark A. Hofer; Audley A. Ciamporcero, Jr.

[57] ABSTRACT

A diluted whole blood sample is hydrodynamically focused to a given point. A light beam is transversely focused on the same point and the principles of dark field microscopy are utilized, detecting scattered light and thereby discriminating platelets from red blood cells based on cell volume and refractivity.

11 Claims, 5 Drawing Figures

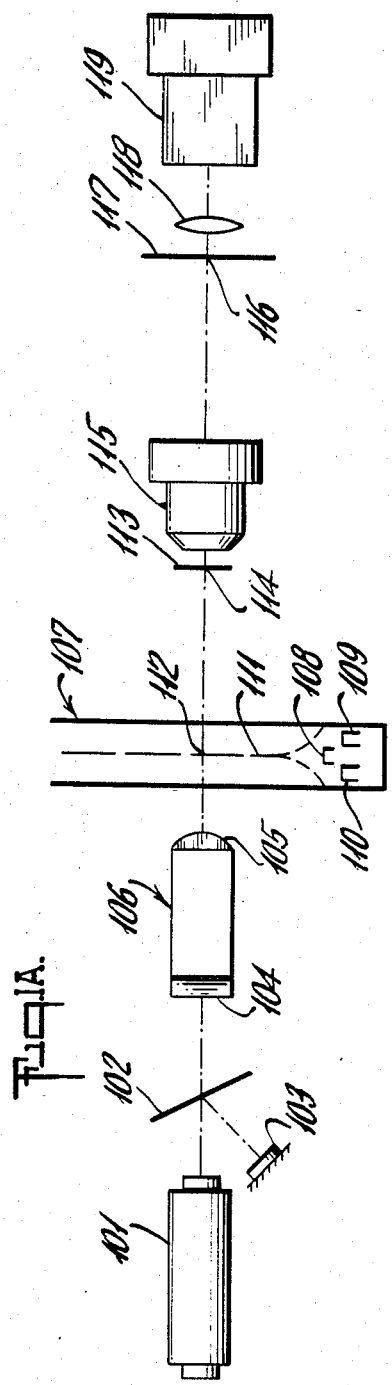
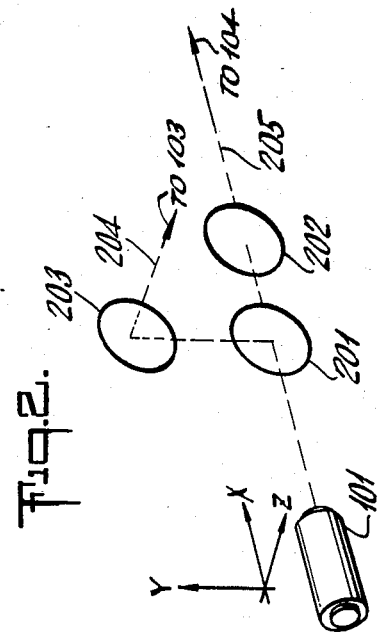
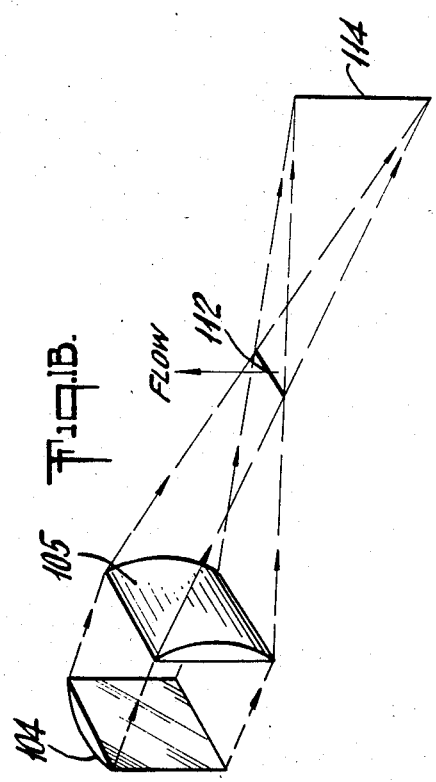
Fig.1A.
Fig.1B.
Fig.2.

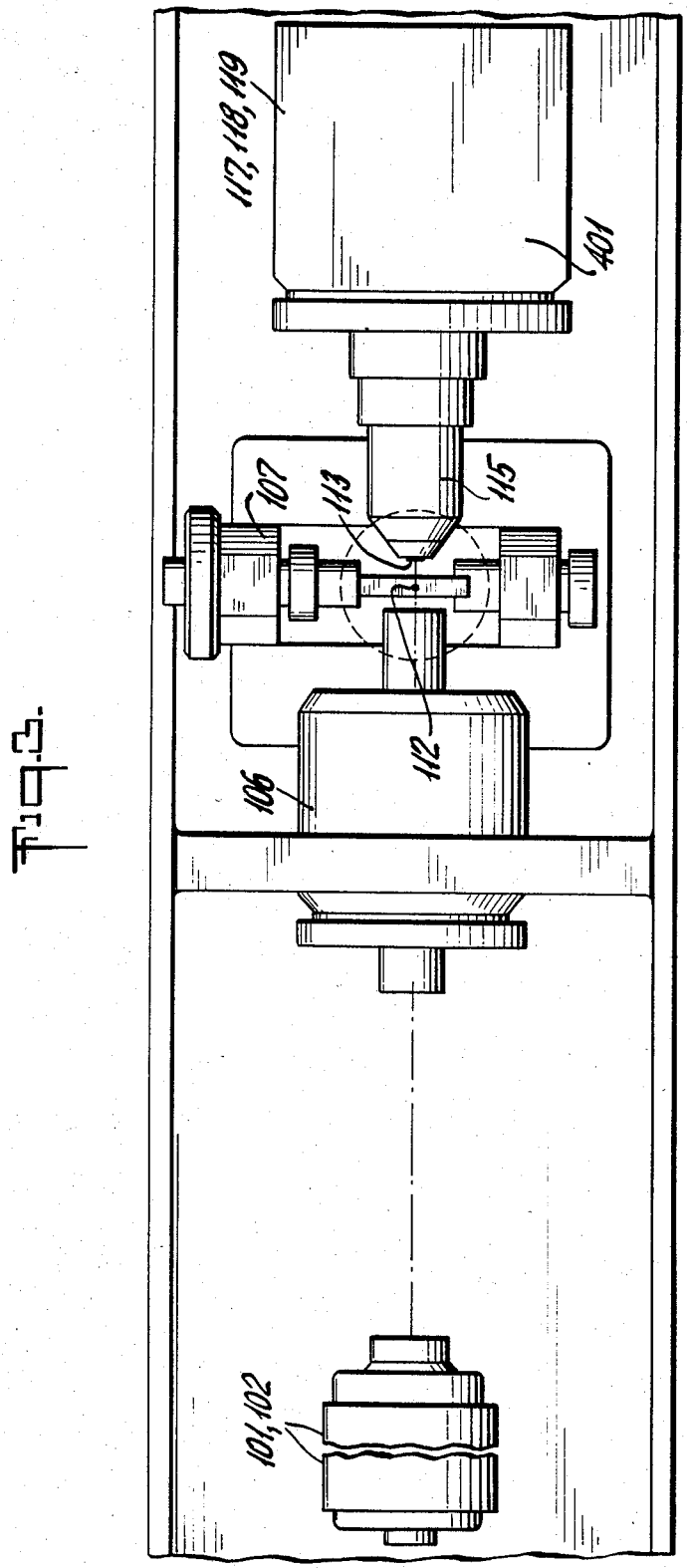

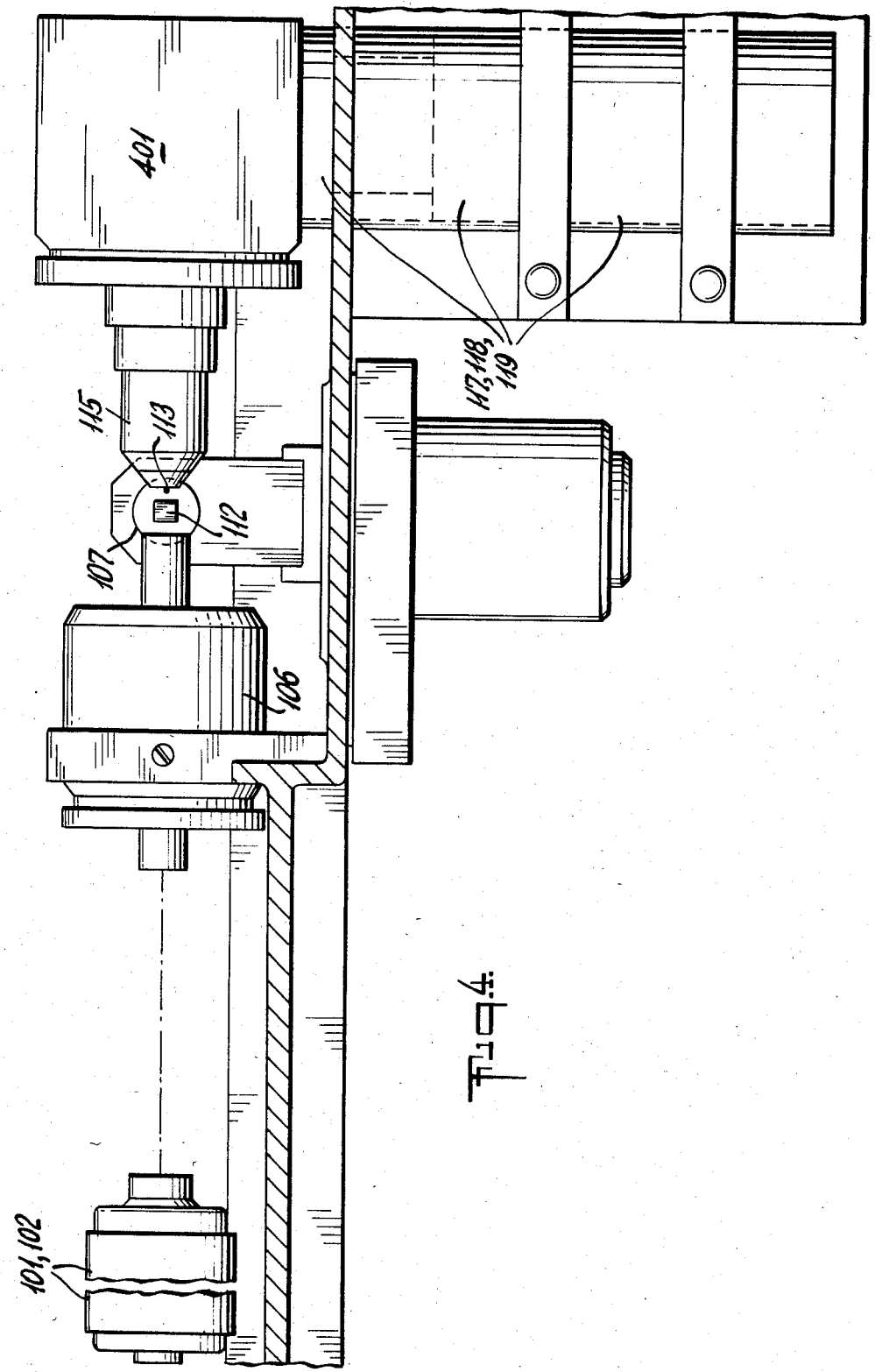

APPARATUS AND METHOD FOR DETECTING PLATELETS IN WHOLE BLOOD

FIELD OF THE INVENTION

This invention relates to blood cell analysis, and more particularly to the detection of platelets in the presence of other cells, such as in whole blood.

PRIOR ART AND BACKGROUND

Modern clinical and research analysis techniques require careful and controlled identification and separation of the various types of cells found in the blood, for example white cells, red cells, and platelets. Typically, small blood samples are taken, appropriately diluted and subjected to various reagents and/or dyes, and the diluted subsamples are appropriately analyzed. Often, histograms are obtained which set forth distributions of various cells as a function of specified parameters, such as volume. Based upon a knowledge of the nature and characteristics of the respective cells, these histograms may often be effectively correlated with the presence of cells of various types.

One challenging problem in the design and production of effective blood analysis instruments has been the discrimination, identification, and analysis of platelets. In particular, by virtue of the size, size distribution, and overall number of platelets per unit volume, substantial discrimination difficulties have been engendered. For example, the smallest of platelets often are confused with particles, microbubbles, or other spurious elements in the diluted blood sample under investigation. The largest of platelets often have a similar volume to that of small red cells, for example in the range of thirty to forty cubic microns. Moreover, the number of platelets per unit volume of blood normally is much smaller than the number of red cells in the same volume, such that if the red cells possess even a normal size distribution, the number of small red cells may be quite comparable to the number of platelets in the sample. Dilution steps generally have little effect on these problems, since red cells, white cells, platelets, and the like are conventional, diluted in the same ratios. In fact, the normal consequence of dilution is that fewer cells overall are available for analysis, thereby tending to increase the severity of the problem.

The principal, and heretofore most generally successful, prior art approach to platelet discrimination and analysis has relied upon principles relating to electrical conductivity or resistance. In accordance with this approach, a pair of electrolyte tanks are maintained adjacent to one another, separated only by an electrically insulating wall. A positive electrode is inserted into one tank, and negative electrode into the other. A small orifice, typically in the range of 50-75 microns in diameter, penetrates the wall, thereby interconnecting the two tanks of electrolyte. A blood sample is inserted into one tank, and by maintenance of flow, passes from one to the other through the orifice. The resistance of the orifice is carefully monitored, and this resistance is changed as cells pass through the orifice, based on different conductivities (or resistances) of different types of cell. Generally, the resistance change as a cell passes through the orifice is a function of the volume and the shape of the cell.

This prior art approach is satisfactory for normal cells and normal platelets, but encounters a rather severe discrimination breakdown with respect to large platelets and small red cells, which possess comparable volumetric parameters. Such problems are further exacerbated by the fact that the actual number of small red cells in a normal sample is comparable to the number of platelets in the sample. Conventional attempts to correct these problems, and to distinguish between small red cells and large platelets, utilize mathematical correction, generally based on the assumption that red cells have a known volume distribution whereas platelets have a different, but known volume distribution. On this basis, algorithms have been derived to correct the actual data and to depict a calculated discrimination between red cells and platelets. These algorithms typically are adequate for non-pathological blood samples, but often are inaccurate for pathological blood samples, or samples which have recently been subject to transfusions.

These prior art systems also encounter difficulties with respect to accurate detection of the smallest of platelets. That is, the prior art electrical resistance type of systems encounter problems with respect to electronic noise, small spurious particles at or near the orifice, or acoustic vibration in the electrolytes. Algorithms have been developed in order to attempt to correct for these difficulties, but it is evident that these algorithms are at best in the nature of estimates, and in fact cannot adequately account universally for particulate, vibratory, and the like difficulties which may be attendant to the installation of the instrument or to the procedures utilized by the technician, and not to any physical or physiologically related factors

DISCLOSURE OF THE INVENTION

It is a primary object of the present invention to discriminate platelets in the presence of other cells, such as in whole blood, adequately avoiding confusion between large platelets and small red cells, and between small platelets and spurious particles or bubbles in the sample.

It is a further object of the present invention to provide such apparatus and methods which rely primarily upon direct measurement, rather than upon extensive correction of measured data by means of algorithms or the like.

It is a still further object to provide apparatus and methods which distinguish platelets from red cells on bases other than merely upon cell volume and shape.

It is a still further object to discriminate platelets by methods other than electrical/conductivity measurements, and thereby to minimize or substantially eliminate electronic problems such as noise.

It is yet another object to provide methods which discriminate platelets from red blood cells in samples having pathological cell conditions, or having had recent transfusion or blood withdrawals, as well as for observation of non-pathological blood samples.

The present invention is grounded on the fundamental proposition of discriminating platelets based on an optical approach, and thereby conditioning the measurement on cell refractivity as well as volume. In so doing, the present invention permits reliance on the different optical characteristics of the cells, which are widely different between red cells and platelets, and thereby which enable a much finer discrimination between red cells and platelets than would be feasible with mere volumetric (i.e. electrical) methods. Utilization of focused optics, and more particularly the principles of dark field microscopy, facilitate consideration of very small, precise local areas, thereby substantially reducing the effect of spurious particles or bubbles nearby the area being considered.

In accordance with the principles of the present invention, a blood sample is maneuvered to pass by a specified point, a cell at a time in rapid succession (i.e. hydrodynamic focusing). This point is illuminated, as is known in the art, with the further stipulation that the illuminating beam be optically processed to impinge on a particular predefined area and along a particular line. The dimensions of the focal spot are made small enough to reduce cell counting coincidence to levels low enough to permit high precision coincident error correction.

As each cell passes through the optical focal region, various fractions of the incident radiation are transmitted, scattered and absorbed by the cell. The transmitted radiation is then physically blocked by a contrived obstruction that matches the incident beam cross-sectional profile, so that only scattered radiation is collected, such as by lens or mirror systems.

The scattered light collection optics is arranged so as to cast an image of the illuminated sample flow stream on an aperture, the same size as the illuminated flow stream image, and the collection optics depth of focus is the size of the sample flow stream. Therefore, only scattered light that originated at the intersection of the incident focused radiation and hydrodyanamically focused sample stream is allowed to pass through the aperture. This radiation is sensed by a photodetector, which in turn produces electrical signals which are easily processed to give indications of the types of cell so illuminated. (e.g. by means of pulse height and pulse width indicative of duration of light detected.)

In accordance with the principles of the present invention, platelets are readily discriminated from red blood cells, even when their respective individual cell volumes are substantially similar. Moreover, principles of careful focusing substantially reduce the effects of spurious matter or bubbles in the focusing fluid (sheath) that surrounds the sample stream, thereby enhancing the ability to discriminate very small platelets.

DESCRIPTION OF THE DRAWINGS

FIGS. 1A and 1B show a schematic representation of an illustrative embodiment of the principles of the present invention;

FIG. 2 shows an alternative beam splitting scheme useful in conjunction with the embodiment of FIG. 1A; and FIGS. 3 and 4 show respective side and top views of a preferred construction for the embodiment of FIGS. 1A and 1B.

BEST MODE FOR CARRYING OUT THE INVENTION

As set forth hereinbefore, the principles of the present invention relate partly to utilization of cell refractivity in order to help discriminate platelets from red blood cells. Expressed mathematically, the refractivity R may be calculated by the equation:

$$R = \frac{n_{cell}}{n_{medium}} - 1,$$

where $n_{cell}$ is the refractive index of the cell in question, and $n_{medium}$ is the refractive index of the diluent or solution in which the cell is suspended.

In the following discussion, reference will mainly be had to FIGS. 1A and 1B which shows symbolically and functionally the principles of the present invention. FIGS. 3 and 4 are labelled with numbers corresponding to particular aspects of the FIGS. 1A and 1B embodiment. It will be understood that FIGS. 3 and 4 are configured in terms of everyday hardware, but that the embodiment of FIGS. 3 and 4 substantially performs the functions attributed to the respective aspects of the FIGS. 1A and 1B embodiment.

In FIGS. 1A and 1B, a laser 101 produces a light beam which is coupled to a beam splitter 102. Laser 101 is of the sort which produces light in the visible spectrum and in the continuous operation mode (i.e. not pulsed). In a preferred embodiment, laser 101 is a commercially available helium neon laser; in practice, however, many alternative lasers will be suitable. In fact, the basic light source in accordance with the principles of the present invention need not be provided as a laser, so long as the source of light utilized is compatible with the optical properties called for hereinafter, and focusable to the extent required in accordance with the following.

The beam of light emergent from laser 101 impinges upon a beam splitter 102, which couples portions of the light respectively to a lens pair 106, and to a photodetector 103. The purpose of photodetector 103 is to provide a signal, based upon which the laser 101 may be regulated, preferably by means of monitoring the laser power. This laser regulation operation is routinely accomplished in accordance with the needs and desires of designers of ordinary skill in the art. The beam splitter 102 is alternatively embodied by any of the many commercially available designs, or by the design set forth in FIG. 2. Essentially, the beam splitter 102, in conjunction with photodetector 103, enables a feedback type regulation scheme whereby a light beam of substantially constant power and intensity is coupled to the lens pair 106.

The lens pair 106 is defined by respective cylindrical lenses 104 and 105, each of which subjects the incident beam to linear convergence along a specific axis, such that the beam emergent from the second lens 105 possess a fixed, definite width and height, and has particular respective image and focal plane locations. Specifically, lens 104 converges its incident light into a beam having a particular designated width. (i.e. in the dimension perpendicular to the surface of FIG. 1) at point 112; the focal plane of lens 104 is at the intersection point 114. Lens 105 is also a cylindrical lens, effectively rotated 90 degrees from the orientation of lens 104, such that lens 105 adjusts the height of its emergent beam to a particular dimension at point 112 (i.e. in the vertical direction in FIG. 1 as shown). The focal plane of lens 105 intersects point 112. Hence, the beam emergent from lens pair 106 has designated dimensions, and is focused in a line at the point 112; in a preferred embodiment, the dimension of the beam at point 112 is approximately 200 microns wide (normal to the drawing of FIG. 1), and 5 microns-high (vertical in the drawing of FIG. 1), and is substantially normal to the horizontal dimension of FIG. 1.

A hydrodynamic focusing flow channel 107 provides that cells under investigation pass point 112 substantially one at a time and in rapid succession. This principle of operation and cell analysis is well-known in the art, for example being exemplified by the line of instruments offered commercially by the assignee hereof under the trade designation "Hemac". Briefly, a sheath liquid such as saline is injected upwardly from nozzles 109 and 110, creating a converging flow which is defined by a tapering flow channel 111. The diluted blood sample under investigation is injected at inlet nozzle 108, and is funnelled into and through flow channel 111, with the result that individual cells pass point 112 in succession to one another. This is known in the trade as "hydrodynamic focusing".

Accordingly, it will be appreciated that there exists a dual focusing or coincidence at point 112, with cells being hydrodynamically focused as they pass by point 112, and the emergent light beam from lens pair 106 being focused at that point to a beam having the dimensions necessary to illuminate the passing cells. This incident light is partially transmitted by a cell, partially scattered by a cell, and a small portion is absorbed by the cell, presumably being converted to other forms of energy. In accordance with the principles of the present invention, the more important component is the light scattered by the cells, which in practical application may be approximately one per cent of the light which illuminates the cell.

In accordance with the present invention, principles of dark field microscopy are utilized to process the light emergent from the cells under investigation at point 112. Generally, these principles involve application of a contrived obstruction which matches the beam profile, such that only scattered light is detected and utilized for analysis of the cell causing the scattering. To this end, in FIG. 1, a wire or the like obstruction 113 is placed in the beam path, the dimensions of the wire 113 being the same, at intersection point 114 as the light beam. For the exemplary embodiment set forth herein, intersection point 114 provides an obstruction approximately 700 microns wide to the beam emergent from point 112. The function of wire 113, therefore, is to block all light transmitted from lens pair 106 directly through point 112. It will be appreciated that substantially all light from lens pair 106 will be blocked by wire 113 when no cell is present at point 112, and that light transmitted by cells at point 112 will be blocked by the wire 113. Hence, only and substantially all light scattered by the cells at point 112 will be passed by obstruction 113 onto a microscope objective 115. While in a preferred embodiment the obstruction 113 is a vertical wire, in alternative embodiments, the obstruction 113 is a vertical photodetector which blocks unscattered light, detects light extinction by cells, and passes the scattered light onto the objective 115.

The purpose of microscope objective 115 is to detect side to side scatter of light from the cells at point 112, which is substantially all such light which is scattered. This light in turn is converged by the objective 115 to point 116, which is an aperture defined by an otherwise opaque screen 117. In a preferred embodiment, the microscope objective 115 is a 10-20×magnification, 0.25 numerical aperture objective of common commercial pedigree; aperture 116 is the size of the magnified image of the beam at point 112.

Screen 117 defines the image plane of microscope objective 115, and aperture 116 therein is located on the axis defined by points 112 and 114 hereinbefore discussed (whether that axis be linear, or optically manipulated as desired). The consequence of locating aperture 116 in the center of the image plane of objective 115 is that only light corresponding to the illuminated cell at 112 will be passed through aperture 116. Hence, the effect of illuminated particles, microbubbles, or other spurious matter in the area near the point 112 will substantially be blocked by the opaque screen 117, and will not be passed to photodetector 119.

Light passing through aperture 116 is coupled to a lens 118, which provides diffuse illumination of a photomultipler 119, which has its sensitive portion located in the focal plane of lens 118. Use of the focal plane, rather than the image plane of lens 118, tends to eliminate irregularities in the sensitivity of the photomultiplier 119. In a preferred embodiment, the photomultiplier 119 is a ten-stage S-20 low dark current photomultiplier, such as for example is commercially available from DuMont, Inc.

Light impinging on the photomultiplier is detected and converted to electrical impulses, which are processed, is desired, to produce histograms or the like corresponding to the cells under investigation. Essentially, the signal from photomultiplier 119 is an analog signal having pulses or peaks corresponding to illumination of individual cells at point 112, the amplitude of the pulses and the width thereof corresponding to the physical configuration of the cell under investigation. It will be apparent that utilization of the optical techniques hereinbefore described, however, cause the signal from photomultiplier 119 to be dependent not only upon the volume of the cells, but also of the cell refractivity, since scattered light is utilized for cell detection purposes.

FIG. 2 shows an illustrative configuration of a beam splitter 102 of FIG. 1. In FIG. 2, the axis of light is shown isometrically, passing from a laser 101 toward lens 104. The embodiment of FIG. 2 utilizes three dielectric mirrors 201, 202, and 203, which divide the light beam from laser 101 into components 204 and 205, irrespective of the polarization of the beam from laser 101. Operation of the mirrors 201, 202, and 203 may be appreciated by consideration of the spatial orientation thereof; to do so, a three-dimensional coordinate system may be employed such as shown. In such a coordinate system, mirror 201, which reflects part of its incident beam to mirror 203, and passes part of its incident beam to mirror 202, is inclined 45° to the X axis and 45° to the Y axis, and 0° to the Z axis. Mirror 203, which reflects part of its incident light in the direction of the Z axis to photodetector 103, is oriented at 45° to the Y axis, 45° to the Z axis, and 0° with respect to the X axis. Mirror 202, which passes part of the incident light but provides a polarization correction comparable to that provided at mirror 203 for beam 204, is oriented at 45° to the X axis, 45° to the Z axis, and 0° to the Y axis. As will be appreciated by those of ordinary skill in the art, beams 204 and 205 will thereby be of proportional intensities that are independent of the polarization state of the beam from 101 with beam 204 being offset from and orthogonal to beam 205.

Referring briefly to FIGS. 3 and 4, an advantageous physical layout is shown for the embodiment of FIG. 1. As noted in FIG. 4, a 45° reflection is employed at 401, thereby conserving overall space. Otherwise, the embodiment of FIGS. 3 and 4 employ the particular physical embodiments of the respective units as set forth as being preferred in connection with the foregoing description of the embodiment of FIG. 1.

It will be understood that the foregoing sets forth illustrative and preferred embodiments of the present invention, but that numerous alternative embodiments will occur to those of ordinary skill in the art without departure from the spirit or scope of the principles of the present invention.

What is claimed is:

1. A method of analyzing blood cells of a sample comprising:
   (a) providing all cells to be analyzed through a predetermined area in a single sample stream analysis;
   (b) illuminating respective blood cells in said sample by providing to said area focused illumination zone which dimensionally accommodates both red cells and platelets;
   (c) detecting light scattered by cells in said zone to the exclusion of other light; and
   (d) discriminating platelets from red blood cells based on the parameters of cell volume and cell refractivity and duration of light so detected.

2. The method of claim 1 wherein said illuminating step comprises:
   (a) passing the cells, one at a time, past a predetermined focal point;
   (b) providing a regulated source of visible light;
   (c) focusing light from said source substantially normally to cell flow to illuminate substantially single cells at said point, said focused light beam haivng a predetermined cross-section at said point.

3. The method of claim 2 wherein said blocking step comprises placing a physical block across the light path emergent from said cells, said block being placed in the focal plane eventuating from said illuminating step.

4. The method of claim 3 wherein said detecting step comprises detecting light emergent from said focal point and not blocked in said placing step.

5. A method as described in claim 1 wherein said illuminating step comprises focusing light normally to a sensing zone through which cells of said sample pass, in sequence, generally normally to incident light, said zone being elongated generally normally both to incident light and to the sample stream.

6. The method of claims 1 or 5 wherein said detecting step comprises:
   (a) detecting substantially low-angle, forward-scattered light from cells;
   (b) blocking substantially all other light from said cells; and wherein said discriminating step comprises discriminating whether a red cell or a platelet scattered the detected light, based on the amplitude and duration of light so detected.

7. A method of analyzing blood cells of a sample comprising:
   (a) providing all cells to be analyzed through a predetermined area in a single sample stream analysis;
   (b) illuminating respective blood cells in said sample by providing to said area a focused illumination zone which dimensionally accommodates both cells and platelets;
   (c) detecting light scattered by cells in said zone to the exclusion of other light; and
   (d) discriminating platelets from red blood cells based on the parameters of cell volume and cell refactivity.

8. The method as provided in claim 7 wherein the detecting step comprises:
   (a) detecting substantially low angle, forward scattered light by said cells; and
   (b) blocking substantially all other light from said illumination zone.

9. The method as provided in claim 8 wherein the blocking step comprises placing a physical block across the light path emergent from said illumination zone.

10. The method as provided in claim 9 wherein the detecting step comprises detecting light emergent from said zone not blocked in said placing step.

11. A method of analyzing blood cells of a sample comprising:
    (a) providing all cells to be analyzed through a predetermined area in a single sample stream analysis;
    (b) illuminating respective blood cells in said sample by providing to said area a focused illumination zone which dimensionally accommodates both cells and platelets;
    (c) detecting light scattered by cells in said zone to the exclusion of other light by blocking substantially nonscattered light and applying said scattered light to a dark field optics system; and
    (d) discriminating platelets from red blood cells based on the parameters of cell volume and cell refractivity.

* * * * *